United States Patent [19]

Adams et al.

[11] Patent Number: 4,840,892

[45] Date of Patent: Jun. 20, 1989

[54] POLYNUCLEOTIDE HYBRIDIZATION PROBES

[75] Inventors: Craig W. Adams, King of Prussia, Pa.; Jeffry J. Leary, Brea, Calif.; Martin Rosenberg, Malvern, Pa.

[73] Assignee: Smithkline Beckman Corporation, Philadelphia, Pa.

[21] Appl. No.: 723,388

[22] Filed: Apr. 15, 1985

Related U.S. Application Data

[63] Continuation-in-part of Ser. No. 610,363, May 15, 1984, abandoned.

[51] Int. Cl.$^4$ .................... C12Q 1/70; C12Q 1/68; C12P 19/34
[52] U.S. Cl. ............................. 435/5; 435/91; 435/6; 536/27; 935/3; 935/6; 935/9; 935/78
[58] Field of Search .................. 435/6, 8, 9, 172.3, 435/810, 91, 5; 436/501, 518; 935/1, 78, 82, 22, 3, 6, 9, 536/27

[56] References Cited

U.S. PATENT DOCUMENTS

| | | | |
|---|---|---|---|
| 4,059,685 | 11/1977 | Johnson | 436/533 |
| 4,358,535 | 11/1982 | Falkow et al. | 435/5 |
| 4,563,417 | 1/1986 | Albarella et al. | 435/6 |
| 4,581,333 | 4/1986 | Kourilsky et al. | 435/6 |
| 4,629,689 | 12/1986 | Diamond et al. | 435/6 |
| 4,687,732 | 8/1987 | Ward | 435/6 |
| 4,687,736 | 8/1987 | Newman et al. | 435/6 |
| 4,719,176 | 1/1988 | Klotz | 435/6 |

OTHER PUBLICATIONS

Messing et al., Crene, 17, pp. 271–277, 1982.
Draper, Nucleic Acid, Research, 12, 989, 1984.

*Primary Examiner*—Esther M. Kepplinger
*Attorney, Agent, or Firm*—Edward T. Lentz; Janice E. Williams; Alan D. Lourie

[57] ABSTRACT

Polynucleotide hybridization probes are labeled in non-probe regions but not in probe regions by selectively protecting probe regions prior to modification of the polynucleotide.

17 Claims, No Drawings

POLYNUCLEOTIDE HYBRIDIZATION PROBES

This application is a continuation-in-part of Application Ser. No. 610,363, filed 05/15/84, abandoned.

FIELD OF THE INVENTION

This invention relates to polynucleotide hybridization probes and, in particular, to improved such probes and preparation thereof.

BACKGROUND OF THE INVENTION

Polynucleotide hybridization probes offer an inexpensive, efficient and rapid means of detecting, localizing and isolating "target" nucleotide sequences for clinical and research purposes. Klausner et al., *Biotechnology*, August 1983:471–478, provide interesting background on polynucleotide hybridization probes, including discussion of preparation and use.

Know methods for preparing polynucleotide hybridization probes and for using such probes are well documented in the literature. See, for example, Southern, *J. Mol. Biol.* 98:503–517 (1975); Falkow et al., U.S. Pat. No. 4,385,535; Leary et al., *Proc. Natl. Acad. Sci.* 80:4045–4049 (1983); Langer-Safer et al., *Proc. Natl. Acad. Sci.* 79:4381–4385 (1982); and Langer et al., *Proc. Natl. Acad. Sci.* 78:6633–6637 (1981); and Kohne, WO84-02721, published July 19, 1984.

As disclosed by these and other references, such known methods for preparing probes typically comprise cloning a probe region into a double stranded DNA plasmid. The plasmid carrying the probe region is labeled, typically by enzymatic polymerization techniques. Such techniques include, for example, nick translation. (Rigby et al., *J. Mol Biol.* 113:237 (1977)); gap-filling (Bourguignon et al., *J. Virol.* 20:290 (1976)); and terminal addition, which techniques are carried out in the presence of modified nucleotide triphosphates. Chemical modification techniques, including those reported in references cited below, can also be used.

Brigati et al., *Virology* 126:32–50 (1983), report that biotin-labeled probes in which biotin is bound to deoxyuridine triphosphate (dUTP) by a long chain (11 or 16 atoms) are advantageous over probes in which the biotin label is bound to the nucleotides by a short chain (4 atoms). The polynucleotide probes are labeled by enzymatic incorporation of biotinylated dUTP by nick translation, using DNA polymerase I.

Ward et al., EP-A-63,879, disclose that label molecules are preferably not bound to positions in a nucleotide ring which would cause interference with hydrogen bonding by a probe to a target sequence. The authors disclose, as a solution to this problem, binding label molecules at the 5-positions of pyrimidines (thymine, cytosine and uracil), at the 7-positions of purines (adenine and guanine), and at the 7-positions of deazapurines. As a further solution, Ward et al. disclose binding label molecules to nucleotides with an extended linker arm, as per Brigati et al., above.

Kourilsky et al., GB No. 2,019,408, disclose chemical modification, by the cytochrome C-biotin technique reported by Manning et al., *Biochem.* 16:1364 (1977), of polynucleotide hybridization probes and labeling of such modified probes prior or subsequent to hybridization to a sample. Chemical labeling methods are also, disclosed by Renz et al., *Nucl. Acids Res.* 12:3435 (1984) and Tchen et al., *Proc. Nat'l. Acad. Sci. USA* 81:3466 (1984). The Renz procedure couples enzymes directly to probes by methods similar to those of Kourilsky et al., GB No. 2,019,408 and Manning et al., cited above. In the Tchen procedure, modification of greater than 5 to 10% of the nucleotide residues adversely affects probe hybridization.

SUMMARY OF THE INVENTION

One aspect of this invention is a method for preparing a polynucleotide hybridization probe which comprises selectively protecting a probe region within a single stranded polynucleotide (DNA or RNA) by hybridizing the probe region to a complementary sequence prior to modifying the polynucleotide. As described below, the probe region is selectively protected by hybridizing the probe region to a complementary oligo or polynucleotide sequence prior to chemically derivatizing, or modifying, bases in the non-probe region by single stranded polynucleotide-specific reactions.

Another aspect of the invention is a polynucleotide hybridization probe prepared by the method of the invention. In particular, in this aspect the invention is a polynucleotide hybridization probe in which the non-probe region has been selectively modified for coupling of label molecules.

Another aspect of the invention is a kit comprising the polynucleotide hybridization probe of the invention.

DETAILED DESCRIPTION OF THE INVENTION

The polynucleotide probes of the invention comprise a probe region, that is, a nucleotide sequence which is complementary to a target sequence, and a non-probe region, that is, a nucleotide sequence which is not complementary to the target sequence.

The target sequence, to which the probe region is complementary, can be any whole or portion of genomic material, or nucleic acid gene product such as ribosomal, transfer, messenger or intron RNA, from an organism, virus or cell. Target sequences are typically in the order of several hundred nucleotides. They can be, for example and without limitation, sequences characteristic of a human or non-human pathogen (which includes any infectious microorganism, virus, or organism including parasites), human or non-human (animal) DNA or RNA sequences such as sequences characteristic of a genetic abnormality or other condition, and sequences derived from genetic engineering experiments such as, for example, total mRNA or random fragments of whole cell DNA. Methods for identifying target sequences and for preparing probe regions are well known, as evidenced by the above-cited references. The target sequence can also be, for example, complementary to a nucleic acid sequence which is charcteristic of a class of human or non-human pathogens, for example, all enteric bacilli or all chlamydia. The target sequence can also be, for example, complementary to a nucleic acid sequence which is characteristic of a host cell or vector used in the manufacture of recombinant DNA products, such as to detect presence of such DNA or RNA contaminant in the product. Hybridization to various RNA types is disclosed, for example, by Kohne, WO84-02721, and Draper, *Nucl. Acids Res.* 13:989 (1984). By "complementary" is meant substantially complementary, that is, having sufficient complementarity to cause the probe region to stably hybridize to the target sequence in selected hybridization conditions.

The non-probe region can be linear or, together with the probe region, can form a covalently closed circle. The non-probe region serves to carry label molecules bound to chemically modified residues. Many label molecules, which are or comprise a detectable moiety, are known and can be used to tag modified bases in the non-probe region of the probe of the invention. The label molecules can be detected directly, or indirectly by contacting the label molecules with another reagent; for example, when the label molecule comprises an enzyme, such other reagent typically would be a colorimetric substrate for the enzyme. Examples of detectable moieties which can be used in label molecules in this invention include, among others, isotopes, haptens, fluorescein, rhodamine and other fluorescent compounds, chemiluminescent groups, lectins, enzymes such as betagalactosidase, antibodies and other proteins whether attached directly or indirectly by bridging techniques. Affinity groups which are useful for coupling detectable moieties to modified residues include biotin and derivatives thereof, such as iminobiotin, which have a strong affinity for avidin.

Polynucleotide molecules used in preparing the probe of the invention can be prepared by known techniques. These include synthetic and biological techniques. Biological synthesis typically involves cloning the molecules whereby multiple copies are "manufactured" by a host microorganism.

Cloning in a single stranded DNA phage, such as the coliphage, M13, is the preferred method for producing probe molecules because, as described below, such cloning allows rapid scale-up and a convenient means of protecting probe regions prior to modification of the non-probe regions. M13 is a filamentous, single stranded DNA virus which is used in recombinant DNA research. Cloning in M13 is described, for example, by Messing, *Meth. Enzymol.* 101:20–77 (1983) and Barnes et al., *Meth. Enzymol.* 101:98–122 (1983), which are incorporated by reference herein as though fully set forth. Other useful single stranded phage include, for example, S13, G4, phiX174; RNA phages such as QB, MS2, R17 and f2; and phage related to M13 such as fd and f1. Other cloning vectors, including plasmids and double stranded phage, can be used, but are less preferred.

Restriction endonuclease cleavage sites which are available for cloning in M13mp10 and M13mp11 include, for example, AccI, BamHI, EcoRI, HincII, HindIII, PstI, SalI, SmaI, SstI and XbaI. Other sites, of course, can be added or substituted. Thus, for example, a BamHI fragment of Hepatitis B Virus, which fragment is about 1300–1400 base pairs and which carries the determinant of the Hepatitis B Virus surface antigen, can be cloned into the BamHI site in M13mp10 or M13mp11 as the probe region. Such viral sequence is characteristic of the Hepatitis B Virus and detection of such in serum or liver biopsy is indicative of Hepatitis B Virus infection. Preferably, though not necessarily, the size of the M13 DNA with the probe region inserted therein is less than about 1000 bases longer than the native M13 DNA.

Prior to modifying the polynucleotide, the probe region is selectively blocked, or protected, so that the probe region will not be substantially modified. In one exemplary embodiment of the invention, this blocking is accomplished by hybridizing a first M13 DNA molecule containing the probe region (herein referred to as M13 probe 1) to a second M13 DNA molecule containing a region which is complementary to the probe region (herein referred to as M13 probe 2). Such molecules can be prepared, for example, by cloning a double stranded DNA fragment which includes the probe region, in both possible orientations within the replicative form of the viral genome, which form is double stranded. Using standard techniques, progeny phage are produced, the progeny having single stranded genomes. Each of the progeny phage carry one of the two strands of probe DNA, that is, one of M13 probe 1 or M13 probe 2. M13 probe 1 and M13 probe 2 are complementary to each other in the probe region, and can be hybridized to each other in order to selectively protect the probe region from derivatization. Either or both resulting polynucleotide molecules can be employed as probes. Or, one of M13 probe 1 and M13 probe 2 can be bound to a solid support prior to carrying out the protection step. This can be accomplished by covalently coupling the DNA, either directly or indirectly, to a solid support. See, for example, Moss et al., *J. Biol. Chem.* 256:12655 (1981). For example, M13 probe 1 can be bound to cellulose. Then, the region is protected by hybridization to M13 probe 2 and the partially double stranded molecules are modified. Following modification, M13 probe 1 and M13 probe 2 are dehybridized such that M13 probe 1 remains bound to the substrate. Phage carrying M13 probes 1 and 2 can also be used as "manufacturers" of additional probes.

Other selective blocking procedures will be apparent to persons ordinarily skilled in the art. For example, a linear polynucleotide having the probe region can be isolated from a recombinant plasmid or double-stranded DNA bacteriophage. Then, the strands can be cut back, for example, 3' to 5', substantially to the probe region by treatment with an exonuclease to produce a probe molecule having a single-stranded non-probe region on surrounding sides of the probe region. The probe region is protected from derivatization because it remains double-stranded.

Having protected the probe region, the intact molecule is modified by one or more single strand-specific reactions, prior to or concurrently with labelling of thusly modified residues. Any single strand-specific, or substantially single strand-specific, modification procedure, which allows a label molecule to be bound to the modified residues, can be used. Preferably, the selected single strand-specific modification procedure results in modification of at least ten-fold more residues in a single stranded polynucleotide or region than in a double stranded polynucleotide or region under specific, identical reaction conditions. After modifying the single strand regions of a polynucleotide probe molecule, any of a number of labels can be bound or coupled to the modified residues before or after hybridization to a sample, as discussed above. Some single strand-specific reactions will result in limited modification of protected residues, but not to such extent that hybridization of the probe region is significantly impaired; in other words, the probe region remains substantially free of label molecules. Preferably, non-probe region residues are modified by biotinylation and label molecules comprise avidin and a detectable moiety. Preferably, the avidin is conjugated to an enzyme.

Single strand-specific modification procedures are known in the art. McMaster et al., *Proc. Natl. Acad. Sci.* 74:4835–4838 (1977), for example, disclose glyoxylation of single stranded polynucleotides. Glyoxal binds primarily to guanadine residues. Resulting polynucleotide cyclic diols can be cleaved by sodium periodate at ambient temperature in aqueous solution to form multiple, reactive dialdehydes on the polynucleotide. The polynucleotide aldehyde can be reacted with, for example, tritiated sodium borohydride to produce a tritiated label, or with a diamine, such as cadaverine, in the presence of sodium borohydride, to prepare a primary amine. Such primary amine can be further reacted with, for example, biotinyl N-hydroxysuccinimide ester to prepare a biotin labeled probe.

In a simplified version of the above, a diamine such as adipic acid dihydrazide is first coupled to biotin with, for example, sulfosuccinimidyl biotin (Pierce Chemical Company). The resulting amine-biotin can then be added directly to periodate oxidized, glyoxalated DNA.

The preferred single strand specific modification procedure is bisulfite catalyzed transamination. Draper, *Nucl. Acids Res.* 12:989 (1984), reports use of this procedure to modify single stranded RNA. See, Example 3, below.

Heterobifunctional agents may also be used to crosslink single stranded DNA or modified single stranded DNA with a label. An example is 4-azidophenylglyoxal which will interact with guanosine in single stranded nucleic acids under mild conditions. The azide functional group thus introduced on DNA will then react with proteins, for example, alkaline phosphatase and fluoroesceinated serum albumin in the presence of ultraviolet light, to accomplish labeling of the nucleic acid. Politz, et al., *Biochem.* 30:372 (1981).

Other single strand-specific modification procedures are well known. A preparer of the probe of the invention can readily select from among such procedures based on needs and convenience. Exemplary modification procedures are described, for example, in "Basic Principles in Nucleic Acid Chemistry", Volume II, Academic Press, 1974, by P.Tso, especially 2–90, by D. M. Brown.

After modification and, optionally, labeling, reactants are removed and the protected probe region is denatured, by known techniques, thereby exposing the probe region for subsequent annealing to a complementary target sequence.

A major advantage of this novel application of single strand-specific chemistry is the ease and efficiency with which the probes can be labeled as compared to conventional enzymatic techniques for probe labeling, including the technique disclosed by Kourilsky et al., GB No. 2,019,408. The technique is extremely amenable to scale-up.

Probes prepared by single strand-specific chemical modification techniques are advantageous because the presence of label does not significantly interfere with hybridization of the probe region to target sequences, thus making such hybridization very efficient. Further, single strand-specific modification can be used to label up to 80 to 90% of all non-probe region bases, whereas by conventional techniques, such extensive labeling can unacceptably interfere with hybridization of the probe region and can be inordinately expensive. Thus, in the probe of the invention, more label can be presented for detection following hybridization. Modification of bases in the non-probe region also reduces background by minimizing non-specific hydrogen bonding of non-probe region bases and stabilizes the probes against degradation such as by the action of nucleases. The probe of the invention need not be labelled only at positions which would minimize interference with hybridization, such as disclosed by Ward et al., EP-A-63,879. In fact, labelling at other positions advantageously further reduces background hybridization, especially to naturally occurring genomic material or nucleic acid gene product which may be complementary to the non-probe region.

The probe of the invention lends itself to packaging in a kit which can consist simply of a container having the probe, such as in a buffered solution, or which can comprise various additional components, in separate containers, useful for using the probe of the invention. The components of the kit will depend upon the intended use of the probe as well as the selection of label molecules. Such kit may comprise the probe and other reagents such as label molecules (if the probe is not pre-labelled), reagents and materials which permit hybridization and detection and/or quantitation of target sequences and reagents and materials for manipulation of target sequences prior to detection. Such kit may comprise the probe of the invention modified with, for example, biotin and directed at DNA or RNA sequences, such as sequences which are specific for human cytomegalovirus, and label molecules, such as an avidin alkaline phosphatase or peroxidase conjugate, such that the enzyme will bind to or otherwise detect hybridized probe molecules. Additionally, a reagent for detecting presence of the label molecules, such as a substrate for the enzyme, preferably a colorimetric substrate, can be included in the kit in a separate container. Such reagent might include, for example, when the label is alkaline phosphatase, solutions of nitroblue tetrazolium in 50% N,N-dimethylformamide; water and 5-bromo, 4-chloro, 3-indolyl phosphate in dimethylformamide. Alternatively, the probe may be pre-labelled such as by biotinylation and coupling of an avidin enzyme conjugate, in which case the kit can include the probe, in one container, and the reagent for detecting presence of the label molecules, in another container. Standards and/or equipment for accurately quantitating the amount of specific probe bound to the target sequences, might also be included. A more elaborate kit can comprise labelled probes specific for 2 or more common etiologic agents of a disease syndrome, such as meningitis or venereal disease. In addition to the label molecules and substrates, this more complex kit might include a plurality of different probes for different target sequences. Such kit could allow identification of an infectious agent as well as classification of the infectious agent into subclasses. Such more complex kit might further comprise equipment and reagents useful for more detailed analysis of the target sequences. For example, analysis of familial genetic disorders or any other genetic traits or tendencies might be examined by restriction and gel electrophoretic analysis of chromosomal DNA derived from a patient. Such kit could include restriction enzymes, restriction enzyme buffers, an electrophoresis matrix (for example, agarose and acrylamide) as well as other reagents for preparing chromosomal DNA, such as reagents for cell lysis and extraction of nucleic acids therefrom, prior to restriction analysis. The above-described components of the kit of the invention are illustrative only. Other reagents and materials and combinations of reagents and materials will be obvious to persons of ordinary skill in the art.

The following examples are illustrative of the invention and not limiting.

EXAMPLE 1

Single Strand-specific Modification

Glyoxylation. Single-stranded M13 CA2 DNA (25 ug in 25 ul of 0.1M $NaPO_4$, pH 7.0) was reacted with 1/5 volume of a deionized 6M aqueous solution of glyoxal at 50° C. for one hour, substantially as described by McMaster et al., *Proc. Natl. Acad. Sci.* 74:4835–4838 (1977), except that dimethyl sulfoxide denaturant was not used. The reaction mixture was diluted to a volume of 100 ul by addition of ice cold $NaPO_4$ buffer (pH 7.0). Resulting modified, that is, glyoxylated, DNA was purified by centrifugal elution through a 1 ml bed of Sephadex G-50 gel (Pharmacia) in 0.1M $NaPO_4$ (pH 7.0).

Periodate Cleavage. Twenty ug of the glyoxylated DNA was converted to reactive aldehyde DNA by periodate cleavage (oxidation) substantially as described by Wilson et al., *Immunofluoresence and Related Staining Techniques*, ed. by Knapp et al., 1978, Elsevier/North Holland Biomedical Press, page 215–224 (1978). Ten ul of 1.0M sodium meta-periodate ($NamIO_4$) at 50° C. was added to the DNA in 90 ul of $NaPO_4$ buffer (pH 7.0) and incubated at ambient temperature (21° C.) for 30 min with occasional shaking. The reaction mixture, containing aldehyde DNA, was then dialysed overnight at 4° C. against three changes of 500 ml of 10 mM $NaPO_4$ (pH 7.0).

Diamine Addition. Cadaverine (1,5-diaminopentane) was coupled to the aldehyde DNA by a technique used for conjugating periodate oxidized glycoprotein enzymes, for example, peroxidase, to epsilon amino groups on immunoglobulin G molecules described by Wilson et al., cited above. Cadaverine free base was diluted to a 1M concentration with 0.5M $NaH_2 PO_4$. Ten ul of the cadaverine solution were added to 90 ul of 0.1M $NaPO_4$ (pH 7.0), containing 10 ug of aldehyde DNA. Schiff's base formation was allowed to proceed for 2 hr at 21° C., pH 12.0, after which the linkage was converted to covalent bonding by reduction with 15 ul of 0.25M $NaBH_4$ in 0.5M NaOH. Reduction was terminated after 2 hr at 4° C. by exclusion chromotographic separation of the DNA product from the small reagents on a 4.5 ml column of P-60 resin (BioRad) in 20 mM $NaPO_4$, 2 mM ethylenediaminetetra-acetate (pH 7.0). Fractions containing the excluded material (cadaverine-labeled DNA) were pooled, dialyzed against 30 mM triethanolamine:acetate (pH 7.6) (TEA), and concentrated by dialysis against dry Sephadex G-200 gel (Pharmacia).

Biotinylation. Available amines of the cadaverine-labeled DNA were biotinylated substantially by the method of Leary et al., *Proc. Natl. Acad. Sci.* 80:4045–4049 (1983) for biotin labeling of alkaline phosphatase. Biotinyl epsilon-aminocaproic acid N-hydroxysuccinimide ester (BACSE), (see, Costello et al., *Clin. Chem.* 25:1572–1580 (1979)) was dissolved in N,N-dimethylformamide to prepare a 20 mg/ml solution of BACSE. Two ul of the solution were added to 1.5 ug of the amine DNA in 150 ul of 30 mM TEA, twice at 30 min intervals, while gently stirring at 4° C. Reaction was terminated after 2.5 hr by addition of 10 ul of Tris:glycine buffer (0.1M Tris, 58 mg/ml glycine, pH 7.9). Biotinylated DNA was purified by exclusion chromatography on P-60 resin as described above. Fractions containing biotin were identified by spotting 1 ul of each fraction on diethylaminoethyl paper and the colorimetric alkaline phosphatase assay of Leary et al., cited above.

The product ($<$3 ug) was confirmed to be single stranded biotinylated DNA by resistance to base hydrolysis, agarose gel mobility, ultraviolet absorbance spectra, and ability to bind avidin:enzyme complexes as per Leary et al., cited above.

The above is illustrative of a procedure for chemically modifying DNA by a single strand-specific reaction. The method can be used to label a polynucleotide probe by first hybridizing the probe region by known techniques, to selectively protect the probe region and then applying single strand-specific chemistry, such as described above. In applying the above-illustrated chemical modification procedure to a polynucleotide having a protected probe region, the diamine addition step is carried out at milder pH, for example, about 8–9, rather than at pH 12, for example, by titration of cadaverine free base to a pH of about 9.5 with 1N HCl and employing neutral solutions of $NaBH_4$.

The probe is used to detect the presence of a specific nucleotide molecule in a research, clinical or industrial sample by known techniques, which include labelling the probe prior or subsequent to hybridization and assaying for hybridization of the probe to the target sequence.

EXAMPLE 2

Comparison of LT Probes

A probe of the invention (A), a second probe which was not modified (B) and a third probe which was modified in the probe and non-probe regions (C) were compared by hybridizing the probes to a first test DNA having no complementarity, a second test DNA having complementarity in the probe region and a third test DNA having complementarity in the non-probe region.

Prior to modifying the probes, the probes were labeled with $^{32}P$, to enable comparison of hybridization, as follows. Single-stranded M13 DNA circles containing a portion (750 bases) of the *E. coli* heat-labile toxin (LT) (M13 probe 1) (10 ug) were linearized by digestion at 0° C. with DNAase 1 (12.5 ng) in 100 ul of 50 mM Tris:HCl, pH7.5, 5 mM $MgCl_2$, 0.05 mg/ml bovine serum albumin. The DNA was then labeled with $^{32}P$ at the 5' termini by standard procedures using gamma $^{32}P$-dATP and polynucleotide kinase (see for example, Maniatis et al., (eds.) 1982, Molecular Cloning, A Laboratory Manual. Cold Spring Harbor Laboratory, Cold Spring Harbor, N.Y. The resulting DNA had a specific radioactivity of $1\times10^7$ dpm/ug, and contained a sequence (the probe region) representing a portion of the *E. coli* labile toxin (LT) gene.

Protection of the probe region. One ug of the $^{32}P$-labeled M13 probe 1 DNA was mixed with 1 ug of single-stranded M13 DNA circles containing a region (750 bases) which was complementary to the probe region in M13 probe 1 (m13 probe 2). The mixtures were heated to 65° C. in 25 ul of 0.1M $NaPO_4$ buffer, pH7.0, for 10 min and allowed to anneal (or hybridize) at 50° C. for one hour, generating the double stranded form of the probe region, the non-probe regions remaining substantially single stranded.

Modification. Probe DNA mixtures generated as above were treated, in the alternative, with buffer alone, 2M glyoxal, or 2M glyoxal plus 50% DMSO at 50° C. for 1 hr in 0.1M $NaPO_4$, pH7.0 to generate, respectively, (A) unmodified polynucleotide probe
(B) probe modified in the non-probe region only, and
(C) probe modified in both non-probe and probe regions.

Hybridization tests. Probes A, B and C were hybridized to five test DNA's (dot blots), as per Leary et al., *Proc. Natl. Acad. Sci.* 80:4045–4049 (1983), by heat denaturation and hybridization on nitrocellulose filters using 25 ng of probe DNA per ml of hybridization buffer containing 50% formamide. Two probes A, one probe B and one probe C (5 ug each) were hybridized to 5 ng, 1 ng, 0.2 ng, 40 pg and 8 pg of each of the test DNA's. The test DNA's are described in the following table.

| test DNA | Number of bases in complementary sequence | location of complementary sequence |
| --- | --- | --- |
| (1) plasmid I | 0 | — |
| (2) plasmid II | 725 | non-probe region |
| (3) plasmid III | 750 | probe region |
| (4) M13 derivative | 7,000 | non-probe region |
| (5) herring sperm | 0 | — |

Hybridization was carried out at 42° C. for 17 hr, after which the filters were washed and exposed to Kodak X-AR X-ray film to identify samples which bound radioactive probe DNA.

Collective results of the hybridization experiment are reported in the following table in which (−) indicates that no hybridization was detected, (+++) indicates very strong hybridization and (+) and (++) indicate weak hybridization and strong hybridization, respectively. (Probe B is the probe of the invention. Probe A is unmodified. Probe C is modified in all regions.)

| Probe | Test DNA | | | | |
| --- | --- | --- | --- | --- | --- |
|  | 1 | 2 | 3 | 4 | 5 |
| A | + | ++ | ++ | +++ | + |
| B | − | − | ++ | + | − |
| C | − | − | − | ± | − |

As indicated, Probe A, the unmodified polynucleotide probe, hybridized very strongly to test DNA 4, strongly to test DNA's 2 and 3 and weakly to test DNA's 1 and 5.

Probe B, the polynucleotide probe modified in the non-probe region, hybridized strongly to test DNA 3, substantially to the same extent as the unmodified probe. An approximate 100 fold reduction in hybridization to test DNA 4, was observed. No hybridization to DNA's 1, 2 or 5 was observed.

Probe C, the polynucleotide probe modified in all regions did not hybridize significantly to any test DNA, with the exception of very weak hybridization to test sample 4.

The single strand-specific modification thus lowered non-specific hybridization to non-probe region complementary sequences or unrelated sequences by approximately 2 orders of magnitude while maintaining the ability of the probe region to hybridize to the target sequence.

EXAMPLE 3

Preparation of Human Beta-globin Gene Probes

A probe of the invention specific for the human beta-globin gene was labeled with the hapten, dinitrophenol (DNP), using the method of the invention.

Protection of the probe region.

Eighty-five ug of single-stranded M13 probe 1 DNA (M13 strain mp1017) containing 1310 bases complementary to the beta-globin gene were mixed with 85 ug of single-stranded M13 probe 2 DNA (M13 strain mp1135) in 0.4 ml of solution containing 10 mM ethylenediamine tetracetate (EDTA) pH 8.0; 0.6M NaCl and 0.06M sodium citrate. The mixture was heated to 100 C for 2 minutes and allowed to hybridize at 65 C for 3 hours. The protected probe DNA was subsequently purified by twice precipitating with ethanol and finally dissolved in 0.16 ml of 10 mM NaPO$_4$, 1.0 mM EDTA pH 7.0.

Modification

The protected probe DNA was modified by bisulfite-catalyzed transamination with ethylene diamine essentially as described by Draper, *Nucl. Acids Res.* 12:989 (1984) and as outlined below.

Fifty ul of DNA mixture were mixed with 0.45 ml of a solution of Na$_2$S$_2$O$_5$ (1.59M) and ethylene diamine (2.8M) at pH 6.0. The mixture was incubated at 42° C. for 1.5 hours and then chilled on ice. The pH was adjusted to 8–8.5 by the addition of 60 ul of 0.5N NaOH and incubation on ice was continued for 30 minutes. The ethylene amine-labeled DNA was separated from the reactants by dialyzing against 30 mM triethanolamine buffer, pH 7.6.

Covalent attachment of the DNP hapten to the amine adduct was accomplished by dissolving 25 mg of DNP-N-hydroxysuccinimide ester in 0.5 ml of dimethylformamide, and adding 10 ul of this reagent to the 0.6 ml of dialysed, amine-labeled DNA, and incubating at room temperature for 1 hour. The DNP-labeled DNA was then purified from the reactants by extracting the mixture 6 times with an equal volumn of chloroform:isoamyl alcohol (24:1) and precipitation of the aqueous phase with ethanol. The final yellow DNA precipitate was dissolved in 100 ul of 10 mM Tris: HCl, 1 mM EDTA, pH 7.5. Biotin-labeled DNA probes were similarly prepared by using biotinyl-aminocaproyl-N-hydroxysuccinimide ester rather than DNP-N-hydroxysuccinimide ester.

Hybridization tests.

Hybridization was determined by alterations in electrophoretic mobility in agarose gels after mixing probe and target DNAs and incubating at standard hybridization conditions. The DNP-labeled probe was shown to hybridize to a plasmid (pHBC6) containing human beta-globin gene sequences, Fukumaki et al., *Cell* 28:585 (1982), but did not hybridize to DNA samples complementary to the non-probe region of the probes.

Detecting DNP-labeled probes.

DNP-labeled DNA was serially diluted in 0.6M NaCl, 0.06M sodium citrate and bound to nitrocellulose filter sheets using a Minifold "Slot-Blot" apparatus (Schleicher and Schuell, Keene, New Hampshire). The location of DNP-labeled DNA was determined using antiserum against DNP (Gateway Immunosera Co., St. Louis, Mo.) and alkalin phosphatase-conjugated goat anti-rabbit IgG (Cappel Labs., Cochranville, Pa.) essentially as described by Tchen et al., *Proc. Natl. Acid Sci.*

U.S. 81:3466 (1984) for DNA modified by another hapten (AAIF). A detection sensitivity of less than 50 pg of DNP-labeled DNA was achieved.

Although the invention and its preferred embodiments are fully disclosed above, it is understood that the invention encompasses all procedures and modifications coming within the scope of the following claims.

We claim:

1. A method for preparing a polynucleotide hybridization probe which comprises selectively protecting a probe region within a single stranded polynucleotide having a probe region and a non-probe region both 5' and 3' to the probe region by hybridizing the probe region to a complementary sequence and then chemically modifying the non-probe region of the remaining single-stranded portion of the polynucleotide.

2. The method of claim 1 in which the single stranded polynucleotide is bound, directly or indirectly, to a solid support prior to selectively protecting the probe region.

3. The method of claim 1 which comprises modifying the probe by transamination after selectively protecting the probe region.

4. The method of claim 1 which comprises modifying the probe by biotinylation after selectively protecting the probe region.

5. The method of claim 4 in which the modified residues are labelled with a label comprising avidin conjugated to a detectable moiety.

6. The method of claim 1 in which the probe region is complementary to a human DNA or RNA sequence or to a characteristic nucleic acid sequence of a human pathogen or of a class of human pathogens.

7. The method of claim 1 in which the probe region is complementary to a non-human DNA or RNA sequence or to a characteristic nucleic acid sequence of a non-human pathogen or of a class of non-human pathogens.

8. The method of claim 1 in which the probe region is complementary to a DNA or RNA sequence characteristic of a host cell or of a vector used in the manufacture of a recombinant DNA product.

9. The method of claim 1 in which the probe is single stranded phage DNA or RNA having a probe region therein.

10. The method of claim 9 in which the single stranded phage DNA or RNA is M13 DNA.

11. The method of claim 10 in which the single stranded polynucleotide is bound, directly or indirectly, to a solid support prior to selectively protecting the probe region.

12. The method of claim 10 which comprises modifying the probe by transamination after selectively protecting the probe region.

13. The method of claim 10 which comprises modifying the probe by biotinylatio after selectively protecting the probe region.

14. The method of claim 13 in which the modified residues are labelled with a label comprising avidin conjugated to a detectable moiety.

15. The method of claim 10 in which the probe region is complementary to a human DNA or RNA sequence or to a characteristic nucleic acid sequence of a human pathogen or of a class of human pathogens.

16. The method of claim 10 in which the probe region is complementary to a non-human DNA or RNA sequence or to a characteristic nucleic acid sequence of a non-human pathogen or of a class of non-human pathogens.

17. The method of claim 10 in which the probe region is complementary to a DNA or RNA sequence characteristic of a host cell or of a vector used in the manufacture of a recombinant DNA product.

* * * * *